United States Patent [19]

Shera

[11] Patent Number: 4,793,705
[45] Date of Patent: Dec. 27, 1988

[54] SINGLE MOLECULE TRACKING

[75] Inventor: E. Brooks Shera, Los Alamos, N. Mex.

[73] Assignee: The United States of America as represented by the United States Department of Energy, Washington, D.C.

[21] Appl. No.: 105,376

[22] Filed: Oct. 7, 1987

[51] Int. Cl.$^4$ ............................................. G01N 21/64
[52] U.S. Cl. ................................ 356/318; 250/458.1; 250/459.1; 356/417
[58] Field of Search ....................... 356/317, 318, 417; 250/458.1, 459.1, 461.1, 461.2

[56] References Cited

U.S. PATENT DOCUMENTS 4,698,308  10/1987  Ikeda .............................. 250/458.1 X

OTHER PUBLICATIONS

A. Ashkin et al., "Optical Trapping and Manipulation of Viruses and Bacteria," Science, 235, 1517–1520 (Mar. 1987).
Dinh C. Nguyen et al., "Ultrasensitive Laser-Induced Fluorescence Detection in Hydrodynamically Focused Flows," J. Opt. Soc. Am. B, 4, No. 2, 138–143 (Feb. 1987).
Dinh C. Nguyen et al., "Detection of Single Molecules of Phycoerythrin in Hydrodynamically Focused Flows by Laser-Induced Fluorescence," Anal. Chem., 59, 2158 (1987).

Primary Examiner—Vincent P. McGraw
Attorney, Agent, or Firm—Ray G. Wilson; Paul D. Gaetjens; Judson R. Hightower

[57] ABSTRACT

A detection system is provided for identifying individual particles or molecules having characteristic emission in a flow train of the particles in a flow cell. A position sensitive sensor is located adjacent the flow cell in a position effective to detect the emissions from the particles within the flow cell and to assign spatial and temporal coordinates for the detected emissions. A computer is then enabled to predict spatial and temporal coordinates for the particle in the flow train as a function of a first detected emission. Comparison hardware or software then compares subsequent detected spatial and temporal coordinates with the predicted spatial and temporal coordinates to determine whether subsequently detected emissions originate from a particle in the train of particles. In one embodiment, the particles include fluorescent dyes which are excited to fluoresce a spectrum characteristic of the particular particle. Photones are emitted adjacent at least one microchannel plate sensor to enable spatial and temporal coordinates to be assigned. The effect of comparing detected coordinates with predicted coordinates is to define a moving sample volume which effectively precludes the effects of background emissions.

12 Claims, 2 Drawing Sheets

SINGLE MOLECULE TRACKING

This invention is generally related to the detection of microscopic particles and, more particularly, to the detection and identification of single molecules. This invention is the result of a contract with the Department of Energy (Contract No. W-7405-ENG-36).

BACKGROUND OF THE INVENTION

The capability for detecting microscopic particles has been proceeding toward smaller particles. For many applications it is essential that microscopic particles be detected in a liquid-phase environment. Existing techniques, usable in a liquid-phase environment, are based on optical trapping and on flow separation using hydrodynamically focused flows. Molecular identification by laser-induced fluorescence has been used with hydrodynamically focused flows to permit the detection of large and highly fluorescent molecules using conventional photomultiplier tubes to detect the molecule fluorescence.

Optical trapping and manipulation of viruses and bacteria are taught in A. Ashkin et al., "Optical Trapping and Manipulation of Viruses and Bacteria," Science 235, 1517 (1987). Rayleigh- and Mie-sized particles, i.e., a particle size range from about 10 $\mu$m down to a few angstroms, have been trapped using optical forces to confine the particles. The only method of identification taught by Ashkin et al. appears to be a size determination from a scattering comparison with a sphere of known size. Further, a large number of particles are trapped.

A hydrodynamically focused flow system is taught by D. C. Nguyen et al., "Ultrasensitive Laser-Induced Fluorescence Detection in Hydrodynamically Focused Flows," J. Opt. Soc. Am. B4, 138 (1987), and D. C. Nguyen et al., "Detection of Single Molecules of Phycoerythrin in Hydrodynamically Focused Flows by Laser Induced Fluorescence," Anal. Chem. 59, 2158 (1987), incorporated herein by reference. As taught therein, improvements in the optics and reductions in the size of the probe volume provide a sensitivity effective to detect a single species containing the fluorescence equivalent of eight rhodamine-6G chromophores. The detection of single molecules of the highly fluorescent species phycoerythrin is reported.

A variety of modifications are reported to enhance the detection sensitivity of the device, with the improvements being related to conventional optics and flow dynamics, and with a sample volume reduction from 11 pL to 0.6 pL producing a concomitant reduction in detected background radiation. The reported sensitivities do not, however, enable the device to detect individual molecules that might typically be of interest, such as fluorophore-tagged versions of the base molecules that make up the DNA polymer.

Thus, available methods and apparatus for detecting particles in a flow stream do not provide the sensitivity for detecting individual molecules that might typically be encountered in immunofluorescence assay, flow cytometry, liquid chromatography, and similar applications. An agglomeration of molecules might be detected, but single molecules could not then be identified. This lack of capabilities in the art is overcome by the present invention and improved method and apparatus are provided for detecting a single modestly fluorescent molecule.

Accordingly, it is an object of the present invention to reliably detect a single fluorescent molecule.

Another object is to reliably detect single fluorescent molecules with a fluorescence equivalent to flouorescently-labeled versions of the bases forming the DNA polymer.

Yet another object is to provide an increased capability of rejecting background radiation.

One other object is to minimize the resolution limitations inherent in conventional optics while maintaining a large field of view.

SUMMARY OF THE INVENTION

To achieve the foregoing and other objects, and in accordance with the purposes of the present invention, as embodied and broadly described herein, the apparatus of this invention may comprise a molecule detection system for identifying individual molecular characteristic emissions in a train of molecules in a flow cell. A position sensitive sensor means is located effective to detect emissions from molecules within the flow cell and to assign spatial and temporal coordinates for the detected emissions. A computer predicts spatial and temporal coordinates for a molecule in the laminar flow as a function of the detected coordinates of a first detected emission. Comparison means then compares detected spatial and temporal coordinates with the predicted spatial and temporal coordinates to determine whether a detected emission originated from an excited molecule in the train of molecules. Thus, molecular emissions can be distinguished from background emissions and identified with a particular molecule in the sequence.

In another characterization of the present invention, a detection method is provided for identifying individual molecules within a flow cell from characteristic molecular emissions. Molecular emissions from within the flow cell are detected with a position sensitive sensor. Spatial and temporal coordinates are then assigned to the detected emissions. Based on known flow characteristics in the flow cell, spatial and temporal coordinates are predicted for a molecule in the flow as a function of a first detected emission within the flow cell. The detected spatial and temporal coordinates of subsequent emissions are compared with predicted spatial and temporal coordinates to determine whether a detected emission originated from a molecule in the train of molecules. Thus, molecular emissions are distinguished from background events and a single molecule can be identified during passage through the flow cell.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE INVENTION

Figure 1:
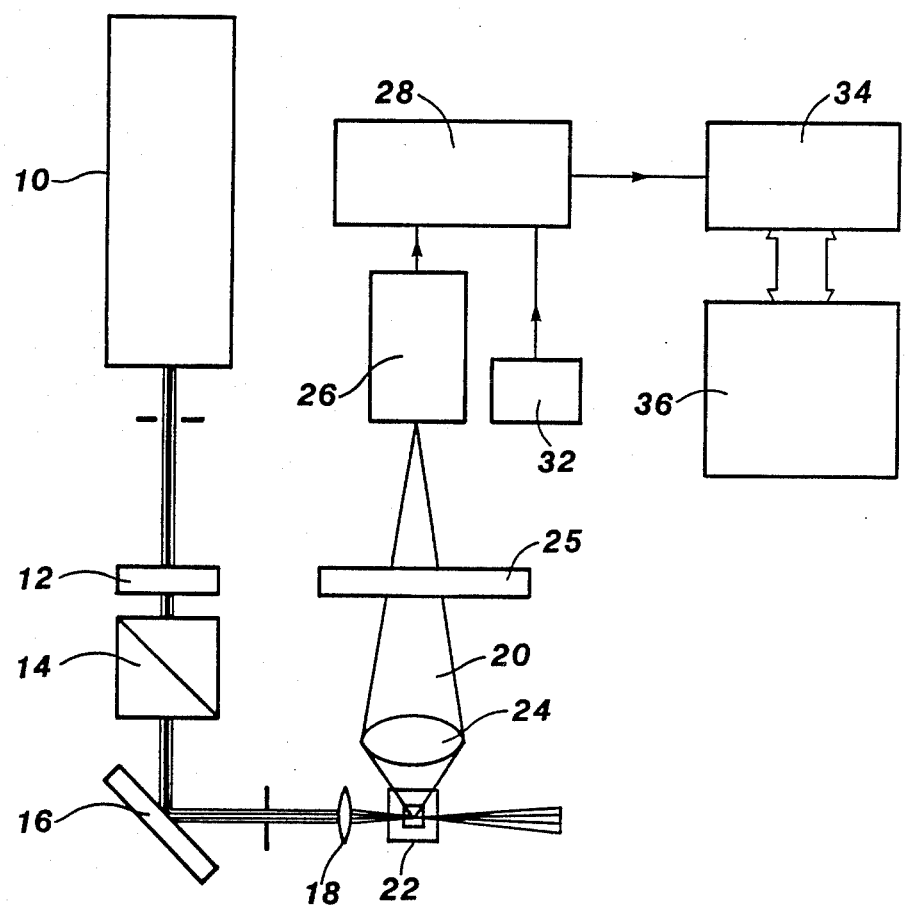
FIG. 1 is a block diagram schematic of the present invention.

Referring now to FIG. 1, there is shown in block diagram schematic form a molecule detection system according to the present invention. The laser excitation system is generally well known and described in the Nguyen et al. articles, hereinabove referenced. Laser 10 is selected with a wavelength effective to fluoresce a selected fluorophore for identifying the molecule to be detected. The output from laser 10 is conventionally passed through half-wave plate 12 and polarizing prism 14, wherein the output power of laser 10 can be adjusted by varying the angle of plate 12 with respect to prism 14. The laser output power and the polarization can be adjusted to minimize background counts.

Figure 2:
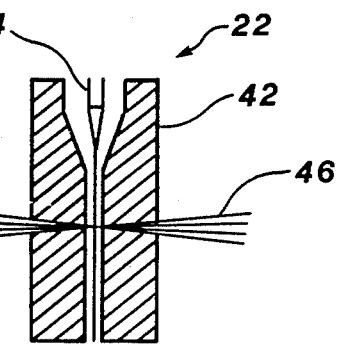
FIG. 2 is a detail of the system flow cell in pictorial form.

Mirror 16 directs the laser beam through lens 18 to focus within flow cell 22 for activating fluorophores attached to molecules in the sample stream. As shown in FIG. 2, sample stream 42 is orthogonal to focused laser beam 46. Sample stream 42 passes within a surrounding hydraulic sheath 44 to provide hydrodynamic focusing of the flow within flow cell 22.

Referring again to FIG. 1, the output from flow cell 22 is optical signal 20 with information on the fluorescing molecules within flow cell 22. Optical signal 20 is focused by microscopic objective lens 24 and filtered by spectral filter 25 to remove wavelengths which are not of interest. The output optical signal is provided to a position-sensitive sensor 26. In one embodiment, position-sensitive detector 26 is formed from a microchannel plate position-sensitive detector (MCP) and operation is hereinafter discussed with respect to a MCP.

A position-sensitive detector of MCP 26 outputs a signal which is indicative of the occurrence of a photon event within flow cell 22 and also location data functionally related to the spatial coordinates of the photon event. Spatial coordinates are provided to digitizer 28 and combined with a temporal input from timer 32 to provide at least a three-dimensional (x, y, t) location for the photon event. Photon event coordinates are output from digitizer 28 to memory 34 for subsequent processing by computer station 36.

Referring now to position-sensitive sensor 26, it is desirable to have the resolution of the system, and related position accuracy, limited by the system optics rather than a MCP. Conventional MCPs may have a positional resolution of 500–1000 pixels in each dimension. If two pixels cover each Rayleigh limit, resolution is limited by the optics and a field of view of 100–200 microns in diameter is provided by objective lens 24. By way of example, the Rayleigh limit at a wavelength of 560 nm is about 0.4 microns. Thus, a position accuracy of 1 micron requires only a precision of ±2 pixels. A suitable MCP is available as model F4146M from ITT, Electro-Optical Products Division.

Digitizer 28 provides spatial and temporal coordinate data in a format that is suitable for direct storage in memory 34 and can operate in real time. Conventional MCP position circuitry digitizes in about 5 $\mu$s. This digitizing interval can be reduced to about 1 $\mu$s, or less, with custom circuitry, if a high data rate operation is desirable. A 1 $\mu$s digitizing interval would enable a maximum photon detection rate of 1 MHz; or, e.g., 170 photons during the transit time predicted by Nguyen et al. for a system comparable to flow cell 22. As discussed below, the detection of only a few photons can provide for reliable molecule identification even with a relatively unsophisticated data reduction algorithm. The flow velocity and laser intensity can readily be adjusted to provide a data rate and observation time suitable for particular applications.

It will be appreciated that the above system provides the position accuracy needed to identify a photon event within 1 micron or less. With a suitable width of the laser beam in the longitudinal direction as, for example, by evanescent wave illumination, this accuracy thus produces an effective sample volume of $10^{-18}$ m$^3$, or $10^{-3}$ $lpL$, a sample volume reduction by about 500 over the 0.6 pL value discussed in Nguyen et al. The effective sample volume allows the system to discriminate against photon events which do not originate with a fluorescing molecule since only a few scattering events will randomly occur within the effective sample volume. The laminar flow provides known trajectories for molecules having a known velocity. Detected photon events can be compared with predicted molecule coordinates and photon events which do not correspond with predicted coordinates can be disregarded. This capability effectively provides a moving sample volume as small as $10^{-3}$ pL within which the presence of a molecule can be reliably predicted.

The above system has been described using a hydrodynamic flow regime and a fluorescing molecule. However, the functional principles apply equally to any dynamic system which can maintain a predictable flow of molecules or small particles in sequence through a detector. Likewise, laser-induced fluorescence is a convenient technique to tag and identify molecules. All that is needed, however, is a detectable emission from the molecule or particle. Alternatively, other molecular emissions, such as electrons, gamma rays, and the like, can be detected by suitable position-sensitive devices. The present invention broadly contemplates hydrodynamic and aerodynamic flow regimes, as well as molecular emissions of all kinds.

Figure 3:
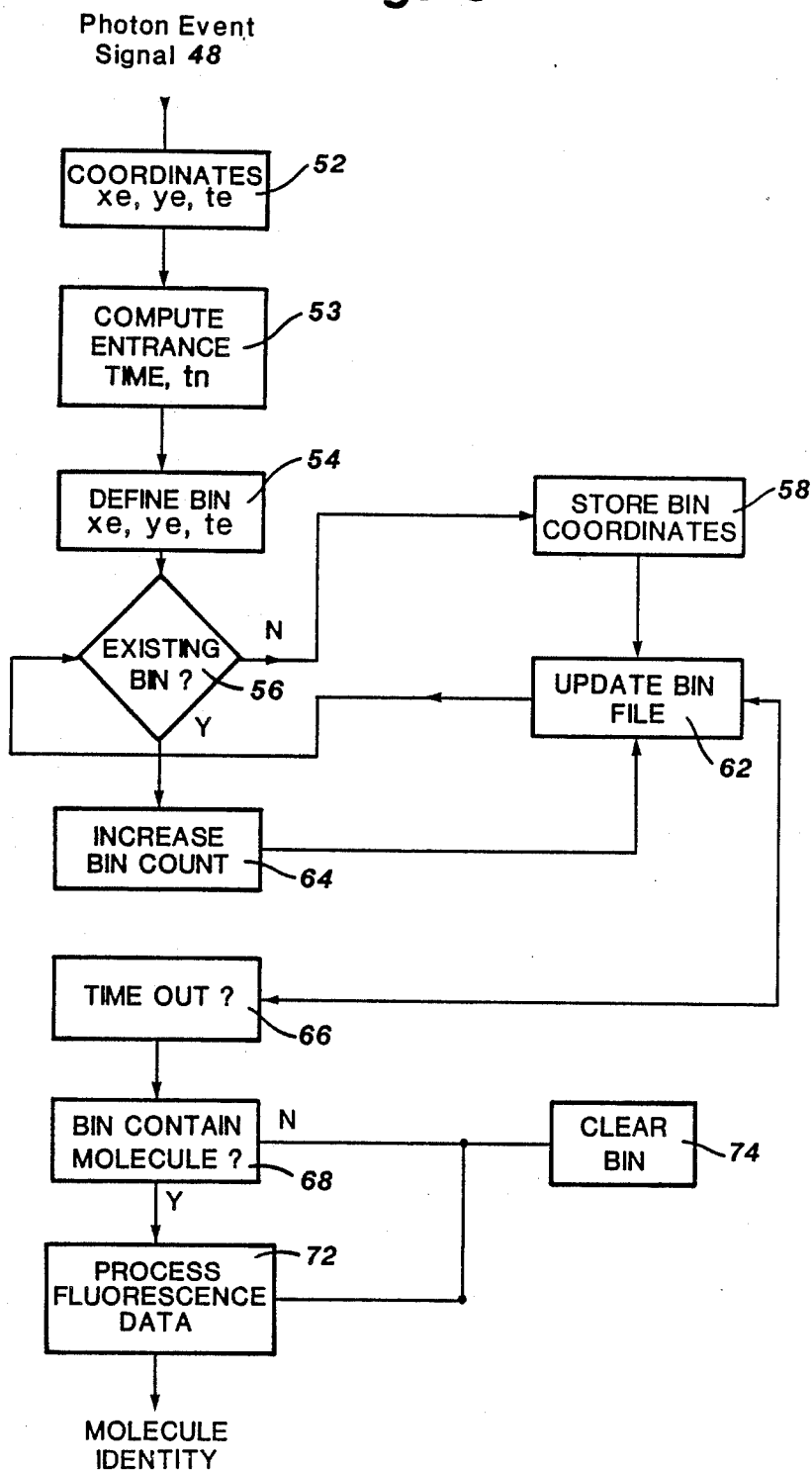
FIG. 3 is flow chart for distinguishing and evaluating individual molecules in the flow cell.

Referring now to FIG. 3, there is shown a flow diagram for exemplary software for determining the presence of a molecule in an effective sample volume. On the occurrence of a photon event 48 from MCP 16 (FIG. 1), the event coordinates ($x_e$, $y_e$, $t_3$) are input 52 and a bin is defined 54 with coordinates $x_e$, $y_e$, $t_n$) where $t_n$ is normalized 53 to the time a molecule having the spatial coordinates would have entered the field of view defined by objective lens 24 (FIG. 1). The new defined bin is compared 56 with existing bins. If the new bin does not exist, the new bin is stored 58 to represent an initial event and the contents of bin file 58 are updated 62.

If existing bin coordinates accommodate the defined event bin coordinates 54, the event is assigned to that particular bin 64. Bins continue to accumulate 64 events until the bin temporal coordinate indicate that the bin has passed outside the field of view of the system.

Timer 66 periodically causes the bins to be examined 68 to determine whether a bin is still within the field of view or whether a molecule was present in that bin. Bins that accumulate a large number of events have a higher probability of containing an actual molecule than bins with fewer events. The small effective sample volume which is provided according to the present invention can produce a clear separation between bins that contain molecules and those that contain only random background events. After the bin count is processed, the bin is cleared 74 for reuse. If the presence of a molecule is indicated, the fluorescence data can be processed 72 for the particular determination being made by the system. More complex data reduction algorithms might further consider diffusion and other departures from laminar flow that can occur in various applications.

The capability to track and identify an individual molecule provides applications which are not possible using conventional photomultiplier tubes. In one important application, the system might be adapted to detect and identify individual bases forming a DNA sequence. A plurality of laser wavelengths, alone or in combination with separate filters 25 and detectors 26 (FIG. 1), could be used to excite individual molecules as they pass through the sample flow cell 22 to identify fluorescent base-specific labels which are attached to the molecules. The track of a molecule will alternately appear or disappear to enable molecule identification during the excitation sequence. Several molecules may be simultaneously present in flow cell 22 and be individually tracked for identification.

While a single MCP system has been discussed above, it may be desirable to provide two orthogonally placed MCPs to increase the number of photons which are collected during transit of the molecule through flow cell 22 and to provide additional spatial information. Detected photon events would be correlated to provide complete three-dimensional spatial coordinates. A detected photon in each of two orthogonally placed detectors will, in principle, enable a trajectory to be predicted, such that the presence of a third photon on the computed four-dimensional trajectory is evidence of a molecule passage.

It will be appreciated that the detection of these few photons in the available transit times produces an infinitesimal probability of missing a molecule entirely. By way of example, in a 2 MCP geometry, and a 170 $\mu$s transit time, shown by Nguyen et al., supra, in Table 3, it can be estimated that each detector will accumulate 8 real and 40 background photons. Thus, the 2 MCPs will detect a mean number of 16 photons, providing a probability of less than $10^{-4}$ of detecting fewer than the 4 photons needed for molecule detection.

The software discussed for FIG. 3 can be provided for each MCP and the bins merged during the processing. A merger determination could be made on the basis of the available common information, i.e., time coordinates. Bins might be examined for merging only after a minimum number of events are accumulated in that bin, thereby assuring that the time coordinates of both bins are sufficiently well determined to make a valid comparison for the merger. The bin with the large number of accumulated events might be selected for the merged bin, whereby all subsequent photon events on the bin trajectory are assigned to a single bin.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A molecule detection system, comprising:
   a flow cell for passing a train of molecules in laminar flow;
   laser means for exciting said molecule to emit photons at a selected wavelength;
   position sensitive sensor means effective to detect said photon emissions within said flow cell and assign spatial and temporal coordinates for said detected photons;
   computer means for predicting spatial and temporal coordinates for a molecule in said laminar flow as a function of a first detected photon; and
   comparison means for comparing said detected spatial and temporal coordinates with said predicted spatial and temporal coordinates to determine whether a detected photon originated from an excited molecule in said train of molecules.

2. A detection system according to claim 1, wherein said position sensitive sensor means includes at least one microchannel plate sensor for outputting said spatial coordinates.

3. A detection system according to claim 1, wherein said position sensitive sensor means has a position accuracy effective for said computer means to create from said predicted coordinates a moving sample volume effective to functionally eliminate background signals from consideration.

4. A detection system for identifying individual molecules having characteristic emissions in a flow train of molecules in a flow cell, comprising:
   position sensitive sensor means effective to detect said emissions from said molecules within said flow cell and assign spatial and temporal coordinates for said detected emissions;
   computer means for predicting spatial and temporal coordinates for a molecule in said flow train as a function of a first detected emission; and
   comparison means for comparing said detected spatial and temporal coordinates with said predicted spatial and temporal coordinates to determine whether subsequently detected emissions originate from an excited molecule in said train of molecules.

5. A detection system according to claim 4, wherein said position sensitive sensor means includes at least one microchannel plate sensor for outputting said spatial coordinates.

6. A detection system according to claim 4, wherein said position sensitive sensor means has a position accuracy effective for said computer means to create from said predicted coordinates a moving sample volume effective to functionally eliminate background signals from consideration.

7. A detection method for identifying individual molecules having a characteristic emission in a flow train, comprising:
   detecting in position sensitive sensor means molecular emissions within said flow train;
   assigning spatial and temporal coordinates for said detected emissions;
   predicting spatial and temporal coordinates for a molecule as a function of a first detected emission; and
   comparing said detected spatial and temporal coordinates with said predicted spatial and temporal coordinates to determine whether subsequently detected emissions originate from a molecule in said train of molecules.

8. A method according to claim 7, wherein detecting emissions includes the step of focusing products from said emissions on at least one microchannel plate sensor.

9. A method according to claim 7, wherein said predicting spacial and temporal coordinates further defines a moving sample window for molecule detection effective to discriminate background emission events from molecule emission events.

10. A method according to claim 7, wherein said emission products are photons.

11. A method according to claim 10, further including the step of irradiating said molecules with a laser to induce a fluorescence for emitting said photons.

12. A method according to claim 7, further including the step of hydrodynamically focusing said flow train within a flow cell.

* * * * *